US00PP16322P2

(12) United States Plant Patent
Geerlings

(10) Patent No.: US PP16,322 P2
(45) Date of Patent: Mar. 7, 2006

(54) ***HELENIUM* PLANT NAMED 'CHELSEY'**

(50) Latin Name: *Helenium hybrida*
Varietal Denomination: Chelsey

(75) Inventor: Nicolaas Petrus Geerlings, Lisse (NL)

(73) Assignee: Witteman + Co., Hillegom (NL)

( * ) Notice: Subject to any disclaimer, the term of this patent is extended or adjusted under 35 U.S.C. 154(b) by 37 days.

(21) Appl. No.: 11/045,986

(22) Filed: Jan. 28, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP11,243 P * 2/2000 Bloom ..... Plt./263
PP15,124 P2 * 8/2004 Brown ..... Plt./263

OTHER PUBLICATIONS

Huxley, Anthony ed. The New Royal Horticultural Society Dictionary of Gardening vol. 2 D to K. 1992 p. 520.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Helenium* plant named 'Chelsey', characterized by its upright and somewhat outwardly spreading plant habit; freely basal branching growth habit; large upright-facing inflorescences with yellow and red bi-colored ray florets; and good garden performance.

2 Drawing Sheets

Botanical designation: *Helenium hybrida.*
Cultivar denomination: 'Chelsey'.

BACKGROUND OF THE INVENTION

The present Invention relates to a new and distinct cultivar of *Helenium* plant, botanically known as *Helenium hybrida*, and hereinafter referred to by the name 'Chelsey'.

The new *Helenium* is a product of a planned breeding program conducted by the Inventor in Lisse, The Netherlands. The objective of the breeding program was to develop *Helenium* cultivars with better growth habit and attractive ray and disc floret coloration.

The new *Helenium* originated from a cross-pollination made by the Inventor in 1999 of the *Helenium hybrida* cultivar Kanaria, not patented, as the female, or seed, parent with an unnamed seedling selection of *Helenium hybrida*, not patented, as the male, or pollen, parent. The cultivar Chelsey was discovered and selected by the Inventor in 2000 as a flowering plant within the progeny of the stated cross-pollination in a controlled environment in Lisse, The Netherlands.

Asexual reproduction of the new *Helenium* by cuttings was first conducted in Lisse, The Netherlands in 2002. Since then, asexual reproduction by cuttings has shown that the unique features of this new *Helenium* are stable and reproduced true to type in successive generations.

SUMMARY OF THE INVENTION

The cultivar Chelsey has not been observed under all possible environmental conditions. The phenotype may vary somewhat with variations in environment such as temperature and light intensity without, however, any variance in genotype.

The following traits have been repeatedly observed and are determined to be the unique characteristics of 'Chelsey'.

These characteristics in combination distinguish 'Chelsey' as a new and distinct *Helenium:*

1. Upright and somewhat outwardly spreading plant habit.
2. Freely basal branching growth habit.
3. Large upright-facing inflorescences with yellow and red bi-colored ray florets.
4. Good garden performance.

Plants of the new *Helenium* differ primarily from plants of the female parent, the cultivar Kanaria, primarily in ray floret coloration as plants of the cultivar Kanaria have solid yellow-colored ray florets. Plants of the new *Helenium* differ primarily from plants of the male parent selection primarily in ray floret coloration as plants of the male parent selection have solid red-colored ray florets.

Plants of the new *Helenium* can be compared to plants of the *Helenium* cultivar Moerheim Beauty, not patented. In side-by-side comparisons conducted in Lisse, The Netherlands, plants of the new *Helenium* differed from plants of the cultivar Moerheim Beauty in the following characteristics:

1. Plants of the new *Helenium* had larger inflorescences than plants of the cultivar Moerheim Beauty.
2. Plants of the new *Helenium* were more freely flowering than plants of the cultivar Moerheim Beauty.
3. Plants of the new *Helenium* and the cultivar Moerheim Beauty differed in ray floret coloration as plants of the cultivar Moerheim Beauty had less intensely-colored ray florets.

BRIEF DESCRIPTION OF THE PHOTOGRAPHS

The accompanying colored photographs illustrate the overall appearance of the new *Helenium* showing the colors as true as it is reasonably possible to obtain in colored reproductions of this type. Colors in the photographs may differ from the color values cited in the detailed botanical description which accurately describe the colors of the new *Helenium.*

The photograph at the top of the first sheet comprises a side perspective view of a typical non-flowering plant of 'Chelsey' grown in a container.

The photograph at the bottom of the first sheet is a close-up view of a typical leaf of 'Chelsey'.

The photograph on the second sheet is a close-up view of a typical inflorescence of 'Chelsey'.

DETAILED BOTANICAL DESCRIPTION

The new *Helenium* has not been observed under all possible environmental conditions. The phenotype may vary somewhat with variations in environment such as temperature and light intensity, without, however, any variance in genotype.

The aforementioned photographs, following observations and measurements describe plants grown in 17-cm containers in Hillegom, The Netherlands, in an outdoor nursery and under commercial production practices. Plants used for the photographs and the description were about one year old. The photographs and description were taken during the late summer with day temperatures ranging from 14 to 31° C. and night temperatures ranging from 4 to 16° C. In the following description, color references are made to The Royal Horticultural Society Colour Chart, 2001 Edition, except where general terms of ordinary dictionary significance are used.

Botanical classification: *Helenium hybrida* cultivar Chelsey.

Parentage:

*Female, or seed, parent.*—*Helenium hybrida* cultivar Kanaria, not patented.

*Male, or pollen, parent.*—Unnamed seedling selection of *Helenium hybrida*, not patented.

Propagation:

*Type.*—By cuttings.

*Time to produce a rooted cutting.*—About two weeks at 9° C.

*Root description.*—Fine; freely branching; white in color.

Plant description:

*Appearance and growth habit.*—Perennial herbaceous container and garden plant. Upright and somewhat outwardly spreading plant habit; narrow inverted triangle. Freely basal branching with about three or four main lateral branches. Moderately vigorous.

*Plant height.*—About 47 cm.

*Plant width or area of spread.*—About 34 cm.

*Lateral branch description.*—Appearance: Mostly rounded with three vertical "wings"; wings about 2.5 mm in height. Length: About 39 cm. Diameter: About 7 mm. Internode length: About 3.4 cm. Strength: Strong. Texture: Smooth, glabrous. Color: 144A; wings, 143A to 143B.

*Foliage description.*—Arrangement: Alternate; simple; sessile. Length: About 14.2 cm. Width: About 3.7 cm. Shape: Narrowly obovate. Apex: Acute. Base: Cuneate; decurrent. Margin: Dentate. Venation pattern: Pinnate. Texture, upper and lower surfaces: Glabrous; slightly rough. Color: Developing foliage, upper surface: 143A. Developing foliage, lower surface: 138A. Fully expanded foliage, upper surface: 137A; venation, 144B. Fully expanded foliage, lower surface: 137C; venation, 144A to 144B.

Inflorescence description:

*Appearance/arrangement.*—Single terminal and axillary inflorescences held above the foliage on strong erect peduncles. Composite inflorescence form, radially symmetrical; flabellate-shaped ray florets; disc florets massed at the center; ray and disc florets develop acropetally on a capitulum. Inflorescences persistent. Inflorescences face mostly upright. Inflorescences mostly flat.

*Flowering response.*—Plants flower continuous and freely from midsummer to late summer in The Netherlands.

*Postproduction longevity.*—Inflorescences maintain good color and substance for about one month on the plant and about two weeks as cut flowers.

*Quantity of inflorescences.*—Freely flowering; about 60 inflorescences per plant develop during the flowering season.

*Fragrance.*—Very faint.

*Inflorescence bud.*—Length: About 8 mm. Diameter: About 2.4 mm. Shape: Flattened globular. Color: N144A.

*Inflorescence size.*—Diameter: About 6.4 cm. Depth (height): About 2.5 cm. Disc diameter: About 2.3 cm. Receptacle height: About 9 mm. Receptacle diameter: About 2.4 cm.

*Ray florets.*—Length: About 3 cm. Width: About 2 cm. Shape: Flabellate. Apex: Three-lobed. Base: Attenuate. Margin: Entire. Texture, upper and lower surfaces: Mostly smooth, towards the base, pubescent. Orientation: Initially upright then perpendicular to the peduncle. Number of ray florets per inflorescence: About 16 in a single whorl. Color: When opening, upper surface: 14A to 14B; towards the base, N163A. When opening, lower surface: 169A or 172A to 34A. Fully opened, upper surface: More intense than N34A to 46A; towards the apex, random marbled sectors, 14A to 14B. Fully opened, lower surface: 178A to 183A.

*Disc florets.*—Shape: Tubular, elongated. Apex: Five-pointed; acute. Length: About 5 mm. Width, apex: About 1.2 mm. Width, base: About 0.8 mm. Number of disc florets per inflorescence: Numerous, about 600. Color, immature: 151A to 151B; towards the apex, 200B. Color, mature: Apex: 200B. Mid-section: 13B to 13C. Base: 151A to 151B.

*Phyllaries.*—Length: About 7 mm. Diameter: About 2 mm. Shape: Linear. Apex: Acute. Base: Cuneate. Margin: Entire. Texture, upper and lower surfaces: Smooth, glabrous; slightly rugose. Number per inflorescence: About 16 in a single whorl. Color, upper surface: 144A to 144B. Color, lower surface: 144B.

*Peduncles.*—Length, terminal peduncle: About 6 cm. Length, fourth peduncle: About 6.8 cm. Length, seventh peduncle: About 7.2 cm. Diameter: About 2 mm. Angle: Mostly erect to about 10° from vertical. Strength: Moderately strong. Texture: Smooth, glabrous. Color: 138A.

*Reproductive organs.*—Androecium: Present on disc florets only. Stamen number: Five per floret. Anther shape: Linear. Anther length: About 1.5 mm. Anther color: 17B. Pollen amount: Scarce. Pollen color: 17B. Gynoecium: Present on both ray and disc florets. Pistil number: One per floret. Pistil length:

About 2.5 mm. Stigma shape: Rounded. Stigma color: 17B to 17C. Style length: About 2 mm. Style color: 154B. Ovary color: 144C.

*Fruit/seed*.—Fruit and seed development have not been observed.

Disease/pest resistance: Resistance to pathogens and pests common to *Helenium* has not been observed on plants grown under outdoor conditions.

Garden performance: Plants of the new *Helenium* have been observed to have good garden performance and to tolerate rain, wind and temperatures from about −10 to 35° C.

It is claimed:

1. A new and distinct cultivar of *Helenium* plant named 'Chelsey', as illustrated and described.

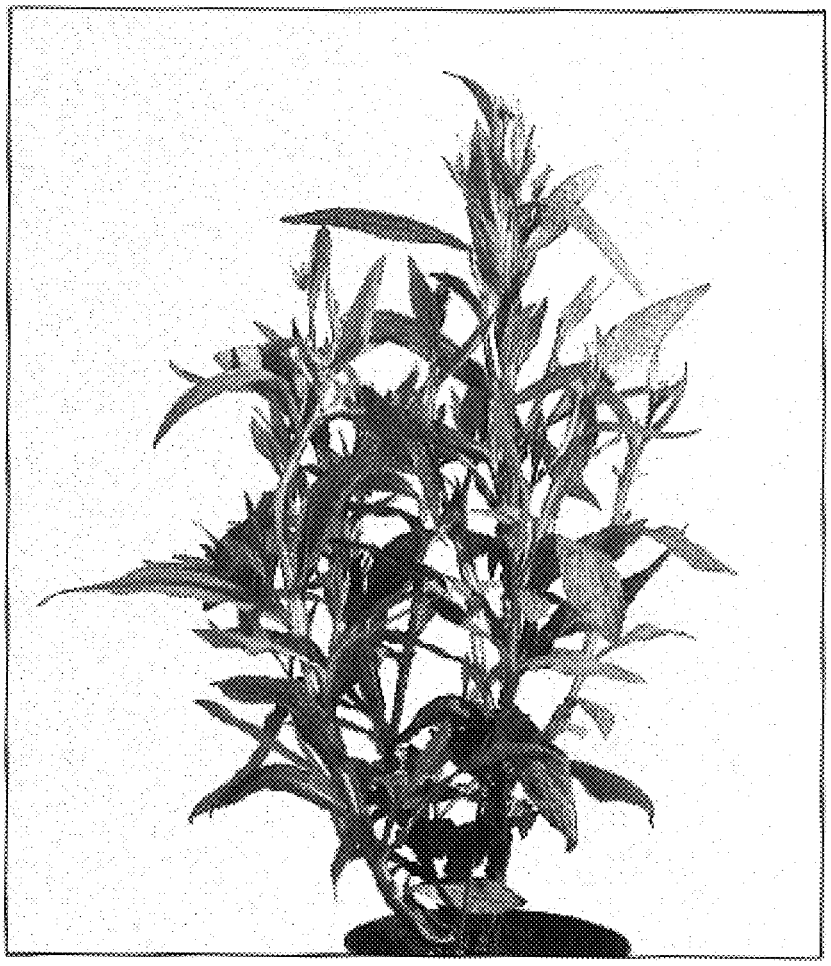
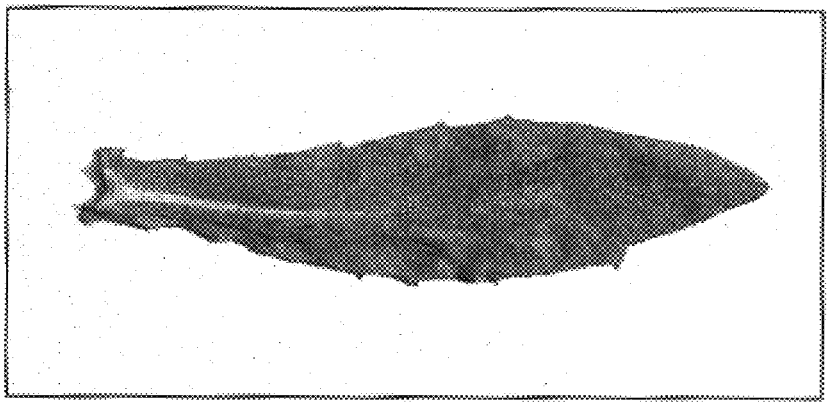

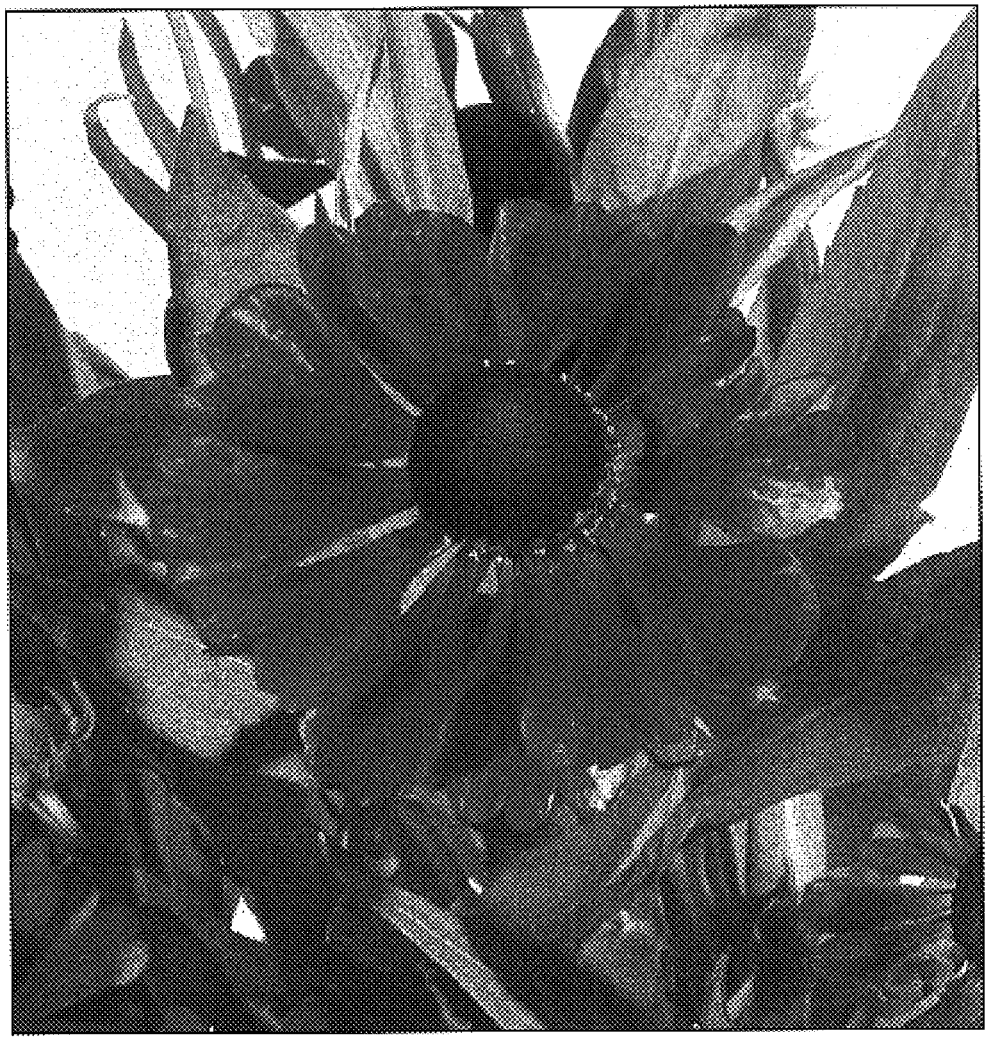

* * * * *